US00PP31359P2

(12) United States Plant Patent
Konst

(10) Patent No.: US PP31,359 P2
(45) Date of Patent: Jan. 14, 2020

(54) ***ALSTROEMERIA* PLANT NAMED 'KONCATIROL'**

(50) Latin Name: *Alstroemeria hybrida*
Varietal Denomination: Koncatirol

(71) Applicant: Johannes Wilhelmus Maria Konst, Nieuwveen (NL)

(72) Inventor: Johannes Wilhelmus Maria Konst, Nieuwveen (NL)

(73) Assignee: Konst Breeding B.V., Nieuwveen (NL)

( * ) Notice: Subject to any disclaimer, the term of this patent is extended or adjusted under 35 U.S.C. 154(b) by 0 days.

(21) Appl. No.: 16/350,809

(22) Filed: Jan. 15, 2019

(51) Int. Cl.
*A01H 5/02* (2018.01)
*A01H 6/00* (2018.01)

(52) U.S. Cl.
USPC ..... Plt./309

(58) Field of Classification Search
USPC ..... Plt./263.1, 309
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Alstroemeria* plant named 'Koncatirol', characterized by its compact and mounding plant habit; sturdy and strong plants; vigorous growth habit and rapid growth rate; freely branching habit; numerous white and yellow green-colored flowers with a light red purple-colored central blush and dark greyed purple-colored stripes; and good garden performance.

2 Drawing Sheets

Botanical designation: *Alstroemeria hybrida.*
Cultivar denomination: 'KONCATIROL'.

BACKGROUND OF THE INVENTION

The present invention relates to a new and distinct cultivar of *Alstroemeria* plant, botanically known as *Alstroemeria hybrida*, typically grown as a container-type garden *Alstroemeria* and hereinafter referred to by the name 'Koncatirol'.

The new *Alstroemeria* plant is a product of a planned breeding program conducted by the Inventor in Nieuwveen, The Netherlands. The objective of the breeding program is to create new compact container-type garden *Alstroemeria* plants that have an early and freely flowering habit with attractive leaf and flower coloration.

The new *Alstroemeria* plant originated from a cross-pollination made by the Inventor in Nieuwveen, The Netherlands in October, 2011 of a proprietary selection of *Alstroemeria hybrida* identified as code number 40293-1, not patented, as the female, or seed, parent with a proprietary selection of *Alstroemeria hybrida* identified as code number 40256-4, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in September, 2013.

Asexual reproduction of the new *Alstroemeria* plant by in vitro rhizogenesis in a controlled greenhouse environment in Nieuwveen, The Netherlands since September, 2015 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncatirol'. These characteristics in combination distinguish 'Koncatirol' as a new and distinct *Alstroemeria* plant:

1. Compact and mounding plant habit.
2. Sturdy and strong plants.
3. Vigorous growth habit and rapid growth rate.
4. Freely branching habit.
5. Numerous white and yellow green-colored flowers with a light red purple-colored central blush and dark greyed purple-colored stripes.
6. Good garden performance.

Plants of the new *Alstroemeria* can be compared to plants of the female parent selection primarily in flower color as plants of the female parent selection have white-colored flowers. In addition, plants of the new *Alstroemeria* are more compact than plants of the female parent selection.

Plants of the new *Alstroemeria* can be compared to plants of the male parent selection. Plants of the new *Alstroemeria* differ primarily from plants of the male parent selection in flower color as plants of the male parent selection have white-colored flowers strongly blushed with reddish pink. In addition, flowers of plants of the new *Alstroemeria* are larger than flowers of plants of the male parent selection.

Plants of the new *Alstroemeria* can be compared to plants of the *Alstroemeria hybrida* 'Koncalucky', disclosed in U.S. Plant Pat. No. 27,994. In side-by-side comparisons, plants of the new *Alstroemeria* differ from plants of 'Koncalucky' in the following characteristics:

1. Plants of the new *Alstroemeria* are more densely foliated than plants of 'Koncalucky'.
2. Plants of the new *Alstroemeria* have taller inflorescences than plants of 'Koncalucky'.

3. Plants of the new *Alstroemeria* flower earlier than plants of 'Koncalucky'.
4. Plants of the new *Alstroemeria* have white and yellow green-colored flowers with a light red purple-colored central blush whereas plants of 'Koncalucky' have white and dark pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Koncatirol' grown in container.

The photograph on the second sheet is a close-up view of typical flowers of 'Koncatirol'.

DETAILED BOTANICAL DESCRIPTION

The aforementioned photographs and following observations and measurements describe plants of the new *Alstroemeria* grown during the winter in 19-cm containers in a glass-covered greenhouse in Nieuwveen, The Netherlands and under cultural practices typical of commercial container-type *Alstroemeria* production. During the production of the plants, day temperatures ranged from 9° C. to 35° C. and night temperatures ranged from 6° C. to 20° C. Plants were 43 weeks old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Koncatirol'.

Parentage:

*Female, or seed, parent*.—Proprietary selection of *Alstroemeria hybrida* identified as code number 40293-1, not patented.

*Male or pollen parent*.—Proprietary selection of *Alstroemeria hybrida* identified as code number 40256-4, not patented.

Propagation:

*Type*.—In vitro rhizogenesis.

*Root description*.—Thick, fleshy; typically white in color, actual color of the roots is dependent on substrate composition, water quality, fertilizers, substrate temperature and physiological age of roots.

*Rooting habit*.—Freely branching; dense.

*Rhizome description*.—Shape: Elongate; rounded. Length: About 6.5 cm. Diameter: About 1.3 cm. Texture: Smooth. Color: Close to 161D.

Plant description:

*Plant and growth habit*.—Perennial garden plant; compact and mounded; freely branching habit, bushy appearance; sturdy and strong plants; vigorous growth habit; rapid growth rate.

*Plant height*.—About 20 cm.

*Plant diameter* (*area of spread*).—About 40 cm.

Stem description:

*Aspect*.—Mostly upright.

*Internode length*.—About 1.2 cm to 1.7 cm.

*Strength*.—Strong, sturdy.

*Texture*.—Smooth, glabrous.

*Color*.—Close to 144D.

Leaf description:

*Arrangement*.—Alternate; below the peduncle, arranged in a single whorl; leaves sessile; about 16 to 22 leaves per lateral branch.

*Length*.—About 2.7 cm to 11.6 cm.

*Width*.—About 0.6 cm to 2.4 cm.

*Shape*.—Lanceolate.

*Apex*.—Acute.

*Base*.—Attenuate.

*Margin*.—Entire.

*Texture and luster, upper and lower surfaces*.—Smooth, glabrous; matte.

*Venation pattern*.—Parallel.

*Color*.—Developing leaves, upper and lower surfaces: Close to 137D. Fully expanded leaves, upper surface: Close to 137A; venation, close to 138A. Fully expanded leaves, lower surface: Close to 137B; venation, close to 138A.

Flower description:

*Flower type and habit*.—Single cup-shaped flowers arranged in compound umbels; flowers face upright to outwardly; freely flowering habit with up to 15 flowers developing per inflorescence and about 40 to 80 flowers developing per plant during the flowering season.

*Natural flowering season*.—Flowering continuous from the late spring until the autumn in The Netherlands; early-flowering habit, plants begin flowering about 6 to 16 weeks after stem initiation.

*Fragrance*.—None detected.

*Flower longevity on the plant*.—About one to three weeks, longevity is temperature-dependent; flowers not persistent.

*Flower longevity as a cut flower*.—About one to two weeks, longevity is temperature-dependent; flowers not persistent.

*Flower buds*.—Length: About 3.8 cm to 4.2 cm. Diameter: About 1.6 cm. Shape: Ovoid. Color: Close to NN155D; apex, close to 144A.

*Umbel height*.—About 11 cm.

*Umbel diameter*.—About 13 cm.

*Flower diameter*.—About 5.6 cm.

*Flower depth* (*height*).—About 5.6 cm to 6.6 cm.

*Perianth*.—Arrangement: Six arranged in two whorls, each whorl with two lateral and one median segments. Size, inner perianth: Length, lateral segments: About 6.1 cm. Width, lateral segments: About 1.9 cm. Length, median segment: About 5.2 cm. Width, median segment: About 1.9 cm. Size, outer perianth: Length, lateral segments: About 5.4 cm. Width, lateral segments: About 3.4 cm. Length, median segment: About 5.4 cm. Width, median segment: About 3.3 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Emarginate, wishbone-shaped. Base, inner and outer perianths, lateral and median segments: Attenuate. Margin, inner perianth, lateral and median segments: Proximally, entire; distally, crenulate. Margin, outer perianth, lateral and median segments: Proximally, entire; distally, crenulate. Texture and luster, inner and outer perianths, lateral and median segments: Smooth, glabrous; matte, dull. Color, inner perianth, lateral segments: When opening, upper surface: Close to N155A; center, close to 150C; towards the base, close to 62D; stripes, close to 183B. When opening, lower surface: Close to N155A; center, close to 150C; apex, close to 144A; towards the base, close to 62D; stripes, close to 183B. Fully opened, upper surface: Close to N155A; center, close to 150C; towards the base, close to 62D; stripes, close to 183B; color does not change with development. Fully opened, lower surface: Close to N155A; center, close to 150C; towards the base, close to 62B; stripes, close to 183B; color does not change with development. Color, inner perianth, median segment: When opening, upper and lower surfaces: Close to N155A; center, close to 183C. Fully opened, upper surface: Close to N155A; apex, close to 144A; stripes, close to 183C; color does not change with development. Fully opened, lower surface: Close to N155A; towards the base, close to 62D; stripes, close to 183C; color does not change with development. Color, outer perianth, lateral segments: When opening and fully opened, upper surface: Close to N155A; towards the apex, close to 144A; towards the base, close to 65B; color does not change with development. When opening and fully opened, lower surface: Close to N155A; towards the apex, close to 144A; towards the base, close to 63C; color does not change with development. Color, outer perianth, median segment: When opening and fully opened, upper surface: Close to N155A; towards the apex, close to 144A; towards the base, close to 65B; color does not change with development. When opening and fully opened, lower surface: Close to N155A; towards the apex, close to 144A; towards the base, close to 63C; color does not change with development.

*Pedicels*.—Length: About 1.8 cm to 3.3 cm. Diameter: About 2 mm to 2.5 mm. Strength: Strong. Angle: About 10° to 30° from vertical. Texture: Smooth, glabrous. Color, upper and lower surfaces: Close to 138C.

*Reproductive organs*.—Stamens: Quantity per flower: Six. Anther shape: Oval. Anther size: About 3 mm by 6.5 mm. Anther color: Close to 197A. Pollen amount: Abundant. Pollen color: Close to N200A. Pistils: Quantity per flower: One. Pistil length: About 4.8 cm. Style length: About 3.7 cm. Style color: Close to 63C. Stigma color: Close to 63B. Ovary color: Close to 138B.

*Fruits and seeds*.—To date, fruit and seed development has not been observed on plants of the new *Alstroemeria*.

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncatirol' as illustrated and described.

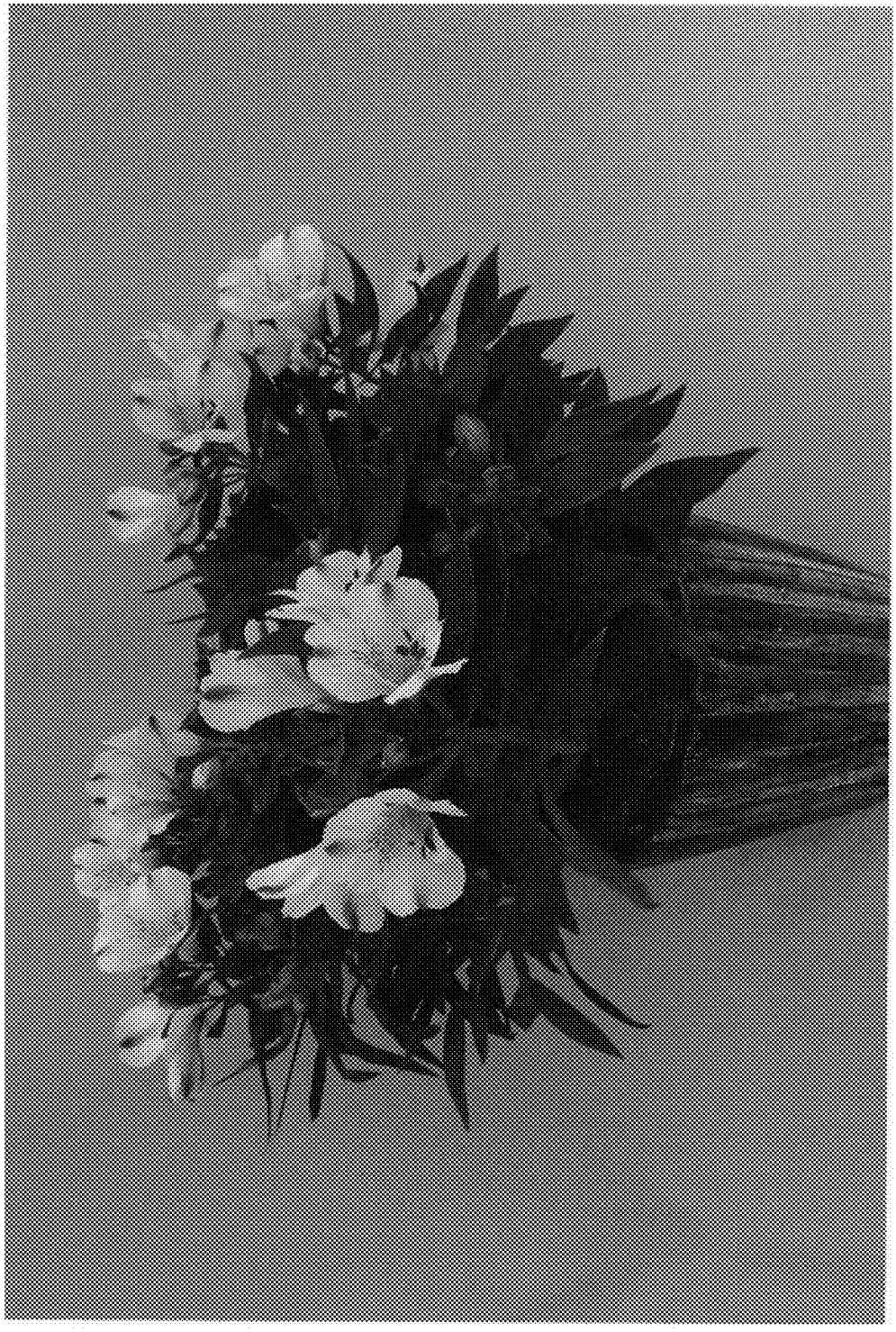

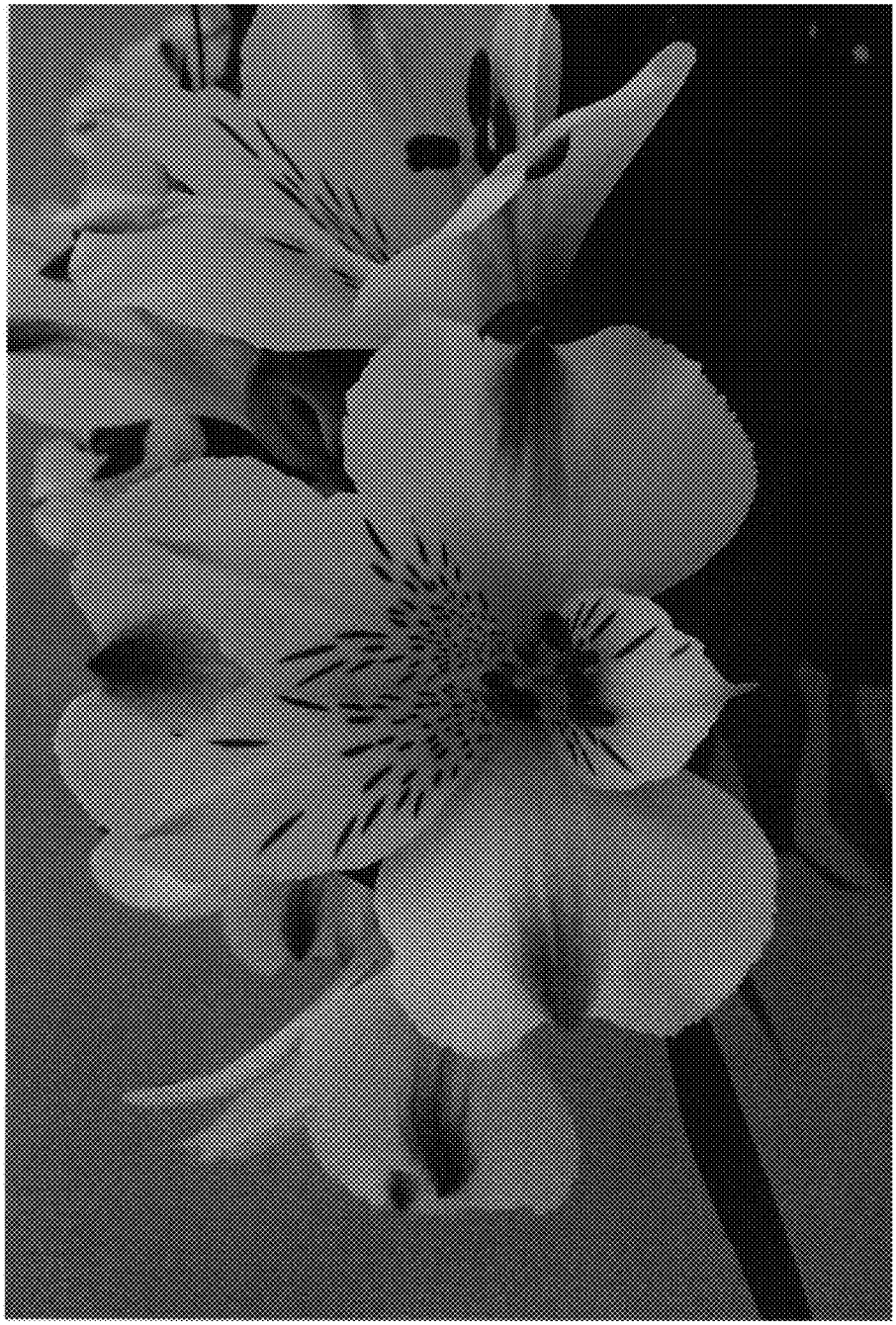

* * * * *